United States Patent [19]

Malcolm et al.

[11] Patent Number: 5,057,571
[45] Date of Patent: Oct. 15, 1991

[54] DISPOSABLE ARTICLE CONSTRUCTION ADHESIVE

[75] Inventors: David B. Malcolm, Maplewood; William L. Bunnelle, Hugo Township, Washington County, Minn.

[73] Assignee: H. B. Fuller Licensing & Financing Inc., Wilmington, Del.

[21] Appl. No.: 594,603

[22] Filed: Oct. 9, 1990

Related U.S. Application Data

[62] Division of Ser. No. 268,003, Nov. 7, 1988, Pat. No. 5,024,667.

[51] Int. Cl.$^5$ .............................................. C08L 53/00
[52] U.S. Cl. .................................... 524/505; 524/271; 524/274
[58] Field of Search ........................ 524/271, 274, 505

[56] References Cited

U.S. PATENT DOCUMENTS

| | | | |
|---|---|---|---|
| 3,239,478 | 3/1966 | Harlan | 260/27 |
| 3,639,521 | 2/1972 | Haleh | 260/880 |
| 3,700,633 | 10/1972 | Wald et al. | 260/890 |
| 3,787,531 | 1/1974 | Dahlquist et al. | 260/876 B |
| 3,837,994 | 9/1974 | Flanagan | 161/100 |
| 3,860,003 | 1/1975 | Buell | 128/287 |
| 3,917,607 | 11/1975 | Crossland et al. | 260/28.5 B |
| 3,932,327 | 1/1976 | Naylor | 260/33.6 A |
| 3,993,613 | 11/1976 | Doss et al. | 260/27 R |
| 4,028,292 | 6/1977 | Korpman | 260/27 R |
| 4,050,462 | 9/1977 | Woon et al. | 128/287 |
| 4,089,824 | 5/1978 | Bronstort et al. | 260/27 R |
| 4,136,699 | 1/1979 | Collins et al. | 128/290 R |
| 4,147,580 | 4/1979 | Buell | 156/291 |
| 4,212,910 | 7/1980 | Taylor et al. | 428/35 |
| 4,253,461 | 3/1981 | Strickland et al. | 128/287 |
| 4,326,528 | 4/1982 | Ryan et al. | 128/287 |
| 4,378,445 | 3/1983 | Brasen et al. | 524/284 |
| 4,392,862 | 7/1983 | Marsan et al. | 604/366 |
| 4,397,645 | 8/1983 | Buell | 604/380 |
| 4,419,494 | 12/1983 | Puletti et al. | 525/95 |
| 4,460,364 | 7/1984 | Chen et al. | 604/387 |
| 4,460,728 | 7/1984 | Schmidt, Jr. et al. | 524/271 |
| 4,526,577 | 7/1985 | Schmidt, Jr. et al. | 604/366 |
| 4,531,945 | 7/1985 | Allison | 604/378 |
| 4,627,847 | 12/1986 | Puletti et al. | 604/366 |
| 4,681,793 | 7/1987 | Linman et al. | 428/138 |
| 4,687,478 | 8/1987 | Van Tilburg | 604/387 |

FOREIGN PATENT DOCUMENTS

0156257A3 3/1985 European Pat. Off.
0249979A2 12/1987 European Pat. Off.
1193626 6/1970 United Kingdom.

OTHER PUBLICATIONS

B. J. Davis, "The Chemistry of C$_5$ Resins," Nippon Zeon of America Ltd., (1979) New York, New York.
"Machinery and Equipment," Plastics Compounding, (1987/1988) Redbook, pp. 98–115.
William H. Korcz, "Liquid Resin Injection System for Continuous Mixing of HMPSA," pp. 81–89 (1981), Hot Melt Adhesives and Coatings.
T. E. Sedlack, "Extruder Performance Over Broad Melt Index Ranges," pp. 27–30, (1983), Paper Synthetics Conference.
H. Kuroki, "Advance in Production and Coating Technology for Hot Melt Pressure Sensitive Adhesives," pp. 33–40, (1981), Hot Melt Adhesives and Coatings.
P. Franz, "Continuous Compounding of Hotmelt Adhesives," pp. 95–104, (1981), Hot Melt Adhesives and Coatings.
R. L. Adams, "Technical Aspects for Extrusion Compounding of Hot Melt Adhesives," pp. 55–65, (1979), Hot Melts An Overview for Management.
W. N. Nissle, "Twin Screw Extruder Processing of Adhesives," pp. 28–32, (1979), Hot Melts An Overview for Management.
P. Franz, "Continuous Production of Hotmelt Adhesives, Aspects of Quality and Costing," pp. 40–54, (1979), Hot Melts An Overview for Management.
Brochures: Welding Engineers, Inc.; Egan Machinery Company, Buxx-Condux, Inc.; Werner & Pfleidereer; Conair; and Black Clawson.

Primary Examiner—James J. Bell
Attorney, Agent, or Firm—Merchant, Gould, Smith, Edell, Welter & Schmidt

[57] ABSTRACT

The composite articles of this invention can be made more efficiently through the use of a single adhesive having sufficient resistance to creep, sufficiently high bond strength, and a viscosity that is controllable through a range permitting it to be used for elastic attachment and in fine line, multi-line extrusion or sprayed adhesive preparation techniques.

10 Claims, No Drawings

DISPOSABLE ARTICLE CONSTRUCTION ADHESIVE

This is a division of application Ser. No. 07/268,003, filed Nov. 7, 1988, now U.S. Pat. No. 5,024,667.

FIELD OF THE INVENTION

The invention relates to a hot melt construction adhesive and to a disposable composite article made by adhesively joining its components. The invention more particularly relates to a disposable article such as a disposable diaper, an incontinent pad, a bed pad, or a feminine pad, made by adhesively bonding a layer such as a film, a woven or nonwoven fabric, a tissue or sheet, or an elastic band to a substrate using the novel adhesive of the invention. The adhesive of the invention has superior adhesion and cohesion, unexpected resistance to creep, high construction bonding strength, heat resistance, and a viscosity profile designed for both elastic attachment and assembly processes including extrusion bonding, fine line construction, multi-line construction or spray application in disposable article technology.

More particularly, the invention relates to disposable diapers that can be constructed using extrusion, spray and multi-line techniques to join a layer to a substrate, or to join an elastic band to a substrate using the adhesive of the invention.

BACKGROUND OF THE INVENTION

The typical commercially used disposable article adhesive uses a plasticizing oil, a tackifying resin in combination with typically a styrene-butadiene-styrene (S-B-S) or styrene-isoprene-styrene (S-I-S) linear (A-B-A) block or a multi-block (A-B-A-B-A-B) copolymer having a molecular weight less than about 140,000. Such conventional commercial adhesives are typically formulated to contain about 20 wt % S-I-S or S-B-S, A-B-A block copolymer, preferably 25 to 35 wt % with 40 to 60 wt % tackifier and 25 to 35 wt % oil. Amounts of A-B-A block copolymer ranging from 20–35 wt % of the adhesive are required to maintain cohesive strength and adhesion to enhance the creep resistance properties in linear A-B-A block copolymer systems when used in the elastic attachment mode. The use of this amount of A-B-A rubber in these formulas result in high costs when compared to other adhesive systems. Additionally, such an adhesive with a high polymer content can result in a product viscosity that is in excess of the maximum viscosity used in the multi-line article construction. Such an adhesive with a lower polymer level (i.e. about 20 wt %) that has a viscosity in the multi-line article construction range can lose cohesive strength, adhesion or creep resistance and can often fail in the elastic attachment mode.

Disposable articles and their manufacture from construction materials including woven and nonwoven fabrics, films and adhesives are described in a variety of U.S. Pat. Nos. Buell, 3,860,003, Woon et al, 4,050,462, Strickland et al, 4,253,461, and Ryan et al, 4,326,528 teach disposable diaper construction. Such diapers typically comprise a fluid impervious backing sheet and absorbent materials applied to the backing sheet. Such diapers typically also comprise an elastic band attached to the . portion of the diaper forming the leg opening. The absorbent material and the elastic bands are attached to the poly impervious backing sheet with hot melt adhesives.

Puletti et al, U.S. Pat. No. 4,419,494 teaches the use of S-B-S linear A-B-A block copolymers in conjunction with a fatty acid polyamide in heat resistant hot melt adhesives for use in the elastic attachment mode. Roeder, U.S. Pat. No. 3,672,371, Allison, U.S. Pat. No. 4,531,945, and VanTilberg, U.S. Pat. No. 4,687,478 teach various aspects of sanitary absorbent articles. Such articles typically comprise a fluid impervious back sheet with an absorbent layer attached thereto. Such absorbent articles can have a pervious top sheet over the absorbent layer and also can be fully wrapped by a pervious outer wrap. Such constructions are made using hot melt adhesives. et al, U.S. Pat. No. 4,392,862, Buell, U.S. Pat. No. 4,396,645 and Lindman et al, U.S. Pat. No. 4,681,793 teach a variety of absorbent devices and their materials and methods of construction. Collins et al, U.S. Pat. No. 4,136,699 teaches an A-B-A block copolymer based construction and positioning adhesive for absorbent articles.

Schmidt, Jr. et al, U.S. Pat. No. 4,526,577 is primarily directed to the use of styrene-butadiene-styrene linear A-B- block and linear A-B-A-B-A-B multi-block copolymers in hot melt adhesives in the manufacture of disposable laminates using multi-line extrusion adhesive application technology. Schmidt, Jr. et al teach that hot melt adhesives have found a wide range of uses, however while a particular hot melt adhesive may have adequate bonding in a particular use, it may be completely unsuitable for other uses or applications. Of the many various hot melt adhesive compositions that have been proposed for use in construction of disposable articles, the use of a particular hot-melt adhesive is dependent on its properties, particularly its ability to bond to polyethylene or polypropylene films, tissue, absorbent materials, and elastic banding.

The primary focus of the Schmidt patent is directed to bonding laminates with linear A-B-A and linear multi-block A-B-A-B-A-B block copolymers which are specifically disclosed and claimed in the patent. Schmidt does not appear to teach elastic band attachment. Only the multi-block A-B-A-B-A-B polymer based adhesives are exemplified in the patent. The patent discloses but does not claim radial or teleblock block copolymers and fails to disclose any aspect of such polymers including molecular weight, percent styrene, percent midblock, percent di-block, molecular weight distribution, or other polymer indicia relevant to adhesive properties and formulation. Further, Schmidt teaches that the adhesive material should contain 15 to 35 wt % of the preferred linear or A-B-A-B-A-B multi-block copolymer and prefers and exemplifies adhesives containing 20 wt % or more of the multi-block copolymer. Additionally, the Schmidt patent prefers relatively high concentrations of styrene, i.e. at levels of at least 35 wt % or as much as 43 wt % styrene in the most preferred A-B-A-B-A-B multi-block copolymer.

The typical S-E-B-S, S-B-S block copolymers identified by the Schmidt et al patent for the adhesives include linear A-B-A block copolymers which range in molecular weight from about 50,000 to about 140,000. The most preferred adhesives contain STEREON 840A, a multi-block A-B-A-B-A-B block copolymer having 35 wt %, or greater, styrene and a molecular weight of about 70,000.

In conventional production of such composite disposable articles, hot melt adhesives are typically extruded at elevated temperatures (about 250°–350° F.) directly onto a work piece, typically a polyethylene or polypropylene film. Additional layers such as a nonwoven fabric, an absorbent material, or a film can be adhered to the poly film substrate using the hot melt adhesive. Spray adhesive technology has been studied and has attracted increasing attention in recent years. However, the predominant application technique mode in production. remains the extruded fine line, multi-dot or multi-line methods.

In adhesive construction of disposable articles a variety of materials are bonded under a wide range of conditions. To optimize performance separate adhesives have evolved for use in the manufacture of premium quality disposable articles. This is particularly true in elastic attachment and in laminate construction. For the most part multi-line construction requires an adhesive with controllable, relatively low viscosity and sufficient bonding strength to maintain the mechanical integrity of the laminate composite article comprising a substrate and an absorbent layer. In sharp contrast to bond elastic materials to substrates, a different adhesive is currently used that primarily exhibits high creep resistance to ensure that the elastic, when under stress, does not move relative to the surface of the substrate or become partially or fully detached. Should the elastic move or become detached, for example in a disposable diaper, the resulting loss of fit could result in inconvenience, waste, embarrassment, discomfort, and associated health and safety problems.

The use of separate adhesives for fine line and for elastic attachment purposes, each having different formulas and properties, increases disposable article manufacturing complexity and can reduce productivity. Additionally, if multiple adhesives are required inventory and storage problems are increased. If the incorrect adhesive is used in the elastic banding it can lead to bond failure. Also, the multi-line extruder nozzle can become plugged. Such problems can lead to inferior products, lost production or both. While some disposable diapers are manufactured with a single adhesive for both multi-line construction and elastic attachment, those diapers are not premium diapers in that they often do not have premium mechanical integrity and can exhibit elastic creep, or detachment.

Accordingly a substantial need exists for a single adhesive having properties rendering the adhesive applicable to both multi-line construction .and elastic bonding applications, which requires a significant advancement in providing improved bond strength, creep resistance and low application viscosity in a single adhesive.

BRIEF DISCUSSION OF THE INVENTION

We have found that surprisingly low levels of a radial block copolymer having a molecular weight of greater than about 140,000, preferably greater than 160,000, can be used to obtain a high level of creep resistance, bond strength, and a low viscosity profile, in a multiple-purpose construction and elastic attachment adhesive. The adhesive exhibits properties qualifying the adhesive for both elastic band attachment and construction applications using multi-line or other disposable article construction techniques.

The radial block copolymer can be blended in amounts that are surprisingly small in comparison to the prior art adhesives, as represented by Schmidt, Jr. et al, U.S. Pat. No. 4,526,577, with appropriate tackifying resins and plasticizing oils. The radial block copolymers of the invention can optionally be combined with linear A-B-A (both S-I-S and S-B-S) block copolymers to produce an adhesive having superior adhesion and cohesion, high bond strength, resistance to creep and resistance to peel when compared to the prior art including the Schmidt patent. The adhesive can have a viscosity profile at application temperatures which typically range from 250°–350° F. useful in both multi-line construction of laminate pieces to polyolefin films and in attachment of elastic to a film.

Radial (or teleblock) copolymers having a molecular weight in excess of about 140,000 are known as shown in the Shell brochure for KRATON .1184. An inspection of the brochure indicates that the material is primarily used as a flexibilizing agent for bituminous compositions such as asphalt. The brochure does not indicate that the materials . are suitable for use as an adhesive composition or any other adhesive related use.

A different type of adhesive is disclosed in Doss et al, U.S. Pat. No. 3,993,613 which teaches an adhesive composition comprising about 10 parts by weight of a rubbery radial teleblock copolymer and a blended tackifier made by mixing a polyterpene, a polyvinyl aromatic or other tackifying resins with a polyalkylene tackifying copolymer. Additionally, Taylor et al, U.S. Pat. No. 4,212,910 teaches a PET bottle base adhesive having 20–40 wt % low molecular weight radial block polymer, 30–59% tackifier and 20–40% wax or oil.

The radial or teleblock copolymers having a molecular weight above 140,000 present significant difficulties in adhesive preparation to manufacturing personnel. While laboratory blending apparatus can be used to manufacture adhesives in small laboratory scale amounts from such radial block copolymers, typical single stage hot melt manufacturing or plant blending techniques, utilized in preparation of prior art adhesives made of typical A-B-A block copolymers and A-B-A-B-A-B multi-block copolymers as represented by Schmidt, Jr., U.S. Pat. No. 4,256,577, fail to adequately blend high molecular weight radial block copolymers with tackifiers or plasticizers into useful adhesive compositions.

Further, the high molecular weight of the radial block copolymers when used at a concentration found in typical adhesive formulations (about 20 wt % and more) results in a viscosity that exceeds production specifications or machine application specifications in typical extrusion, multi-line or fine line construction or elastic attachment methods.

We have found techniques for use with radial or teleblock polymers in hot melt adhesive preparations that permit the rapid and effective preparation of the unique adhesive of the invention. These techniques involve a dual stage or multi-stage process in which a preblend of the high molecular weight radial block copolymers with a lower . molecular weight adhesive component such as either a tackifier, a plasticizer or mixtures thereof, is prepared. The preblend can then be combined with the balance of the adhesive components to form a useful hot melt adhesive composition through a complete intimate blending of the components. We have also found that the adhesive compositions, manufactured with these techniques, have significantly reduced processing time.

The adhesives of this invention can maintain a "T" peel strength of about 100 to 175 gms. at 77° F. (25° C.), S.A.F.T. of about 160° to 190° F., a creep resistance of elastic attachment of about 5 to 30% at 100° F. (38° C.), and exhibit a viscosity of less than about 25,000 centipoise (cP) at 275° F. The articles made with the adhesive are storage stable at 140° F. with little or no delamination and exhibit substrate failure in the dynamic peel adhesion mode.

The radial block copolymers useful in manufacturing the adhesives of the invention have a molecular weight of about 145,000 and have the general formula:

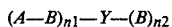
$$(A-B)_{n1}-Y-(B)_{n2}$$

wherein A is a glassy block of a polymerized vinyl substituted aromatic monomer, B is a saturated or unsaturated rubbery block of a polymerized diene having 4-12 carbon atoms, Y is a polyfunctional coupling agent residue, n1 is an integer of at least 3, preferably 3 to 10, most preferably 3 to 5 and n2 is an integer of 0 to 10, most preferably 0 to 4. The end A or mid B blocks can be homo or copolymers of related monomers. Further, at the transition between the blocks some random copolymerization of the A monomers with B monomers can exist.

The preferred rubbers are radial block copolymers having the general formulae

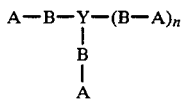

wherein n is 1-3, the A block comprises styrene and the B block comprises butadiene, isoprene, or mixtures thereof which can be hydrogenated. The preferred radial block copolymers contain preferably 15 to 45 wt %, most preferably 25 to 35 wt % of styrene. The average molecular weight of the preferred rubbery block copolymers is at least about 140,000. Most preferably the molecular weight of the block copolymers used in the adhesives of this invention is greater than about 160,000. Currently no radial block copolymer has a molecular weight greater than about 275,000. However we believe increased molecular weights would be beneficial to the adhesives of the invention.

The polyfunctional coupling agents (Y) are well known coupling agents for use in the manufacture of the radial block copolymers of the invention. Such coupling agents and the preparations of the rubbery copolymers useful in the adhesive compositions of the invention are described in detail in a variety of patents including U.S. Pat. No. 3,639,521 and others.

A-B-A block copolymers can be used with the radial block polymers. The A blocks of such A-B-A block copolymer comprise blocks of polymerized vinyl substituted aromatic monomers and the B blocks comprise polymerized dienes having 4-12 carbon atoms. Preferably the A-B-A block copolymers are made of A blocks comprising polymerized styrene and B blocks comprising polymerized butadiene, isoprene or mixtures thereof. Such copolymers typically have a molecular weight in the range of about 70,000-140,000 and have from about 12 to 35 wt % styrene. Such linear and multi-block copolymers are available from Shell Chemical Company, Enichem, Fina and Firestone.

We have found that the adhesive's excellent construction and elastic attachment properties can be improved by stabilizing the oil component of the adhesive. We believe that the migration of oil from the adhesive mass to the bond line between the adhesive and a polyolefin film can cause failure of the adhesive bonds. Stabilizing the oil in the adhesive preventing its migration from the adhesive composition can increase bond strength. We have found that the bond strength can be improved using at least two mechanisms. First a gelling agent can be used which forms an adhesive contained oil gel. The gel effectively locks the oil in place within the adhesive mass, preventing its migration. Additionally, highly oil compatible tackifying agents can be used which through compatibility tend to prevent migration.

TACKIFYING RESIN

The adhesives of the invention contain a tackifying resin in combination with a thermoplastic block copolymer and a plasticizer. Tackifying resins useful in the adhesives of the invention comprise rosin derivatives including wood rosin, tall oil, tall oil derivatives, rosin ester resins, natural and synthetic terpenes and aliphatic or mixed aliphatic-aromatic tackifying resins.

Aromatic monomers useful in forming the aliphatic aromatic resin compositions of this invention can be prepared from any monomer containing substantial aromatic qualities and a polymerizable unsaturated group. Typical examples of such aromatic monomers include the styrenic monomers, styrene, alphamethyl styrene, vinyl toluene, methoxy styrene, tertiary butyl styrene, chlorostyrene, etc., indene monomers including indene, methyl indene and others. Aliphatic monomers are typical natural and synthetic terpenes which contain $C_5$ and $C_6$ cyclohexyl or cyclopentyl saturated groups that can additionally contain a variety of substantial aromatic ring substituents. Aliphatic tackifying resins can be made by polymerizing a feed stream containing sufficient aliphatic monomers such that the resulting resin exhibits aliphatic characteristics. Such feed streams can contain other aliphatic unsaturated monomers such as 1,3-butadiene, cis-1,3-pentadiene, trans-1,3-pentadiene, 2-methyl-1,3-butadiene, 2-methyl-2-butene, cyclopentadiene, dicyclopentadiene, terpene monomers and others. Mixed aliphatic aromatic resins contain sufficient aromatic monomers and sufficient aliphatic monomers and optionally other $C_3$-$C_8$ unsaturated monomers to produce a resin having both aliphatic and aromatic character. The article by Davis, *The Chemistry of $C_5$ Resins*, discusses synthetic $C_5$ resin technology.

The adhesive compositions of the invention can contain rosin and rosin derivatives as a tackifying agent. Rosin is a solid material that occurs naturally in the oleo rosin of pine trees and typically is derived form the oleo resinous exudate of the living tree, from aged stumps and from tall oil produced as a by-product of kraft paper manufacture. After it is obtained rosin can be treated by hydrogenation, dehydrogenation, polymerization, esterification, and other post treatment processes. Rosin is typically classed as a gum rosin, a wood rosin, or as a tall oil rosin which indicate its source The materials can be used unmodified, in the form of esters of polyhydric alcohols, and can be polymerized through the inherent unsaturation of the molecules. Materials are commercially available and can be blended into the adhesive compositions using standard blending techniques. Representative examples of such rosin derivatives include pentaerythritol esters of tall oil, gum rosin, wood rosin, or mixtures thereof.

Representative examples of such aliphatic resins include hydrogenated synthetic $C_9$ resins, synthetic branched and unbranched $C_5$ resins and mixtures thereof. Representative examples of such aromatic tackifying resins include styrenated terpene resins, styrenated C5 resins or mixtures thereof. The selection of tackifying resins is often based on the nature of the B or midblock radial block copolymer. Rosin derivatives are best for S-I-S/S-B-S blends and can be used with either S-I-S or S-B-S alone. Hydrogenated C9 or straight aliphatic resins are preferred for S-I-S copolymers. For S-B-S copolymers, styrenated terpenes or rosin esters are preferred.

PLASTICIZING OILS

Plasticizing oils are used in the construction/elastic attachment adhesives of the invention. Such oils are primarily hydrocarbon oils low in aromatic content. Preferably the oils are paraffinic or naphthenic in character. The oils are preferably low in volatility, are clear and have as little color and odor as possible. The use of a plasticizing oil of this invention also contemplates the use of olefin oligomers, low molecular weight polymers, vegetable oils and their derivatives and similar plasticizing liquids.

OIL GELLING OR COMPLEXING AGENTS

Plasticizing oils used in adhesive compositions can be prevented from migration by the use of gelling or complexing agents which tend to restrain the migration of oil through formations of gels or complexes. The oil can be restrained by a variety of gelling agents including waxes, polyethylene waxes, oxidized waxes, oxidized polyethylene waxes, polyvalent metal soaps, etc.

The following table sets forth the useful, preferred, and most preferred formulas.

TABLE 1

| Ingredient | Useful | Preferred | Most Preferred |
| --- | --- | --- | --- |
| Radial block copolymer* | 5-14 | 7-13 | 8-12 |
| A-B-A block copolymer* | 0-14 | 0-12 | 0-10 |
| Tackifier | 45-85 | 50-80 | 55-75 |
| Plasticizing oil | 5-35 | 6-30 | 8-20 |
| Synthetic polyethylene wax (or other oil complexing agent) | 0-10 | 0.1-9 | 0.25-5 |

*Total polymer content (including both radial block and linear block polymer) is typically about 15 wt % or less of the adhesive.

In sharp contrast to prior art single stage blending procedures for the manufacture of pressure sensitive hot melt disposable article construction adhesives which are represented by Schmidt, Jr. et al, U.S. Pat. No. 4,526,577, we have found that effective commercial manufacture of the hot melt adhesives of this invention using high molecular weight radial block copolymers involves a two-step manufacturing procedure. In the first step the radial block copolymer is mixed at e temperature with at least one additional adhesive component such as a tackifier, plasticizers, or mixtures thereof to form a preblend or a premix wherein the block copolymer is intimately mixed with the other adhesive ingredient. The preblend is then blended with the remaining adhesive components at elevated temperature in standard commercial blending equipment.

In somewhat greater detail, from about 0.5 part of resin to about 2.5 parts of resin can be blended per part of radial block copolymer in order to form the preblend of the invention. The preblends can be prepared in conventional thermoplastic polymer processing equipment capable of providing sufficiently high shear to intimately blend the high molecular weight polymers and the low molecular weight adhesive components such as tackifying resins, oils or other low molecular weight polymeric materials or blends thereof. Examples of such equipment are single or twin screw extruders, intensive internal mixers, Mixtruders, Sigma Blade mixers and the like, which are heated to a sufficient processing temperature, typically between 250°-350° F. If a batch mixer is used the polymer is blended with the adhesive component such as . resin, oil or component blends thereof, typically at an amount less than or equal to the polymer to provide a homogeneous preblend. Thereafter the remaining ingredients can be added and mixed until homogeneous.

The equipment and processes useful in the manufacture of the preblend materials of the invention is described in the following articles. The article "Machinery and Equipment" of *Plastics Compounding Redbook of 1987/88*, is a compilation of information regarding compounding and size reduction equipment including lab and production scale blending apparatus. The articles "Liquid Resin Injection System for Continuous Mixing of HMPSA" and "Extruder Performance Over Broad Melt Index Ranges" discuss blending materials having different viscosity profiles.

The article "Advance in Production and Coating Technology for Hot Melt Pressure Sensitive Adhesives-Multiruder system" discusses the multiruder system of premixer, multiruder and coater and is used for continuous production and coating of hot melt pressure sensitive adhesives for labels and tapes.

The article "Continuous Compounding of Hot Melt Adhesives" discusses continuously operating blending systems capable of blending hot melt adhesives with reduced heat history. Such compounding systems involve extrusion processing.

The article "Technical Aspects for Extrusion Compounding of Hot Melt Adhesives" discusses continuous processing systems for the manufacture of hot melt and pressure sensitive adhesive formulations using batch and twin screw manufacturing methods.

The article "Twin Screw Extruder Process of Adhesive" discusses continuous processing hot melt adhesive compounding with block polymer formulations using multi-stage feeding of oil resins,.additives and base polymer.

The article "Continuous Production of Hot Melt Adhesives Aspects of Quality and Costing" discusses basic processing possibilities for producing hot melts continuously involving working from a premix and deals with four basic continuous processes. The disclosure involves multi-stage addition, pelletizing, coating, etc.. Equipment for such manufacture is shown in the brochures of Welding Engineers, Inc., Eagan Manufacturing Company, Buss-Kneader, Warner and Pfleiderer, Conair and Black Clausen. The disclosures of which relating to equipment and processing are hereby incorporated by reference herein.

We have found that for ease of handling the preblend of the invention can be divided into pieces sized for further processing. We have found that the preblend can be pelletized using a strand, waterface or underwater pelletizer (such as those made by Black Clausen). An underwater pelletizing system can be used in which a water stream removes the cut pellet from the cutting area and directs the water-pellet stream to a centrifugal device that separates the water from the pellet and dries the pellets to a useful format.

The handling properties of the preblend pellets can be improved by treating the surface of the pellets with a nontacky organic or inorganic coating. Such coatings can comprise aqueous dispersions of water insoluble waxes, fatty acid esters, and other known anti-blocking agents. Useful inorganic anti-blocking agents can include such materials as silica, talc, gypsum, calcium oxide, magnesium oxide, etc. One mode of adding the antiblocking agent to the adhesive pellets is in the circulating water in the pelletizing machine. An addition of the antiblocking agent to the water inherently coats the pellets as they are formed at the cutting head with the antiblocking agent which remains after the pellet is separated from the water solution and dried.

The hot melt adhesive of the invention can be manufactured by pillow pelletizing, a procedure such as that disclosed in Franke, U.S. Pat.. Nos. 3,723,035 and 4,054,632. The pillow-shaped pellets can be coated with a nonblocking thermoplastic coating agent. Such coating agents are known, for example EPOLENE C-10 from Eastman Chemical or AC-400 from Allied Chemical, or blends of compatible polymers and additives to control coating viscosity as required to obtain a uniform protective coat. Additionally, the preblend can be extruded in multiple ribbons onto a cooled stainless belt precoated with a compatible thermoplastic coating.

COMPOSITE CONSTRUCTION

Broadly, disposable composite articles such as disposable diapers, feminine protection articles., incontinent pads, bed pads and others are typically made by joining to a substrate, typically a plastic or polyolefin film substrate, an absorbent layer frequently covered by a tissue and a woven or nonwoven overlayer. Elastic banding materials can also be adhesively attached to the plastic film layer between the film and the woven or nonwoven over-layer in articles requiring a close fit around the leg or waist.

Plastic substrates useful in the articles of the invention comprise films made from polyethylene, polypropylene, polyester such as polyethylene terephthalate, polyvinyl chloride, polyvinylidine chloride, polyvinyl acetate, and other materials capable of film formation. The tissue layer is a well known, typically loosely formed cellulosic sheet of high porosity or permeability.

The woven or nonwoven layers can consist of a fluid permeable flexible material that can be made of either hydrophilic or hydrophobic fiber components. The woven and nonwoven webs comprising the fabric can comprise natural or synthetic fibers or mixtures thereof. Woven and nonwoven materials are well known and their construction methods have been practiced for many years. Woven fabrics are typically manufactured in weaving machines forming an interlocking mesh of fibers forming the layer. Nonwoven fabrics can be made through a dry laid or wet laid method in carding processes, air laid processes, or spun bond processes to produce a web that is mechanically, chemically or thermally formed. The fabric layers for use in the composite articles of the invention typically have a basis weight in the range of about 10 to 25, preferably 14 to 18 grams per square yard, a minimum dry tensile of at least 800 grams per centimeter squared in the machine direction, and at least 200 grams per centimeter squared in the cross machine direction.

Synthetic materials commonly used in forming the woven or nonwoven fabric layers include rayon, polyester, polypropylene, polyethylene, nylon and others.

Absorbent layers bonded into the disposable articles of the invention by the adhesive of the invention comprise typically cellulosic pulp or fluff, super-absorbent batts or combinations of fluff and super-absorbent materials. Such fluff layers are often formed and wrapped in tissue to provide mechanical integrity to the fluff which has little inherent mechanical strength. Fluff is typically manufactured through the formation of finely divided cellulosic fibers, however other materials can be used to form highly absorbent fluff or pulp layers.

Elastics or filaments, threads or ribbons of an elastomer or elastic polymer material can be used in the manufacture of the disposable articles of the invention. Such elastomers are polymeric substances with molecular memory. Such materials when placed under stress elongate, but when the stress is relieved, return to their original dimensions. Elastomeric polymers are typically mono or copolymers of moderate molecular weight. Known elastomeric materials include styrene-butadiene copolymers, natural rubbers, isobutylene-isoprene copolymers, polychloroprene systems (NEOPRENE ®, duPont), polyurethanes, polysulfide rubbers, polyacrylate elastomers comprising the copolymerization of ethyl acrylate and acrylic acid-lower alkanol esters, silicone elastomers, fluoro elastomers, ethylene-propylene elastomers, and mixtures thereof. Such elastomers can be crosslinked to increase strength and elastic properties.

In the continuous manufacture of the -disposable articles of this invention and particularly disposable diapers, a small amount of adhesive in the multi-line, multi-dot, fine line, or random pattern is applied by extrusion, wheel or spray application to a thin plastic film substrate. The application occurs at a temperature of about 250°–325° F. and the adhesive is applied at a rate of about 0.1 to 2 mg/lineal inch. The absorbent materials forming the absorbing inner liner of the disposable article is applied to the multi-line adhesive on the film substrate.

In somewhat greater detail, disposable diapers are made in a continuous process by adhering the components of the disposable diaper to a continuous polyethylene or polypropylene film sheet from which the diaper is cut after the individual components are adhered. Typically the components are added in stages including an addition of an elastic, an addition of the absorbent layer, and the optional addition of a waist shield.

In such a technique, thin lines of adhesive are extruded onto the material at a rate of about 0.1 to 2 milligrams per lineal inch of adhesive and the absorbent layers are bonded to the fine lines of adhesive. Such application can be in the form of multi-lines, multi-dots, or other adhesive pattern that can be effectively formed on the poly surface of the film for construction purposes. The absorbent layer is laid down on a continuous web of the poly film.

Elastic bands can be applied to the film layer prior to the absorbent layer or can be applied to the absorbent layer after the layer is bound to the film or the band can be adhesively applied to the outer surface of the film. Elastics are typically applied in a manner such that the elastics provide constriction or stretchable behavior to the edge of the disposable article. Such constricting or elastic behavior provides the disposable article with the property that the disposable article fits or seals itself to the underlying wearer's body surface, generally the leg or the waist. Such constricting or stretchable properties are obtained in one of two ways. The elastic is stretched and adhered to the underlying film. As the stretch on the elastic is released the underlying substrate is gathered. Alternatively, the film substrate can be gathered and unstretched elastic material can be adhesively attached to the peaks of the fluted or gathered film. In this process the elastic needs no stretching since the gathers are preformed.

Elastic attachment is commonly achieved by applying adhesive to the elastic or sprayed over an elastic/poly or elastic/nonwoven composite. The elastic with the adhesive can be applied to the surface of either the poly sheet or nonwoven sheet. The adhesive can be extruded or applied in a spray, in a spiral pattern, in an intermittent pattern or other format. The entire length of the elastic in contact with the poly can be adhered Alternatively, the portion of elastic within about 2-3 inches from the waist band can remain unadhered to the poly layer. The continuous bonded composite article containing poly, absorbent layer and elastic is then cut to form leg openings and to divide the continuous web into individual diapers. Preferably the leg openings are cut with a water jet spray, while the individual diapers are cut with a rotary knife.

Optionally, a waste barrier can be formed in the diaper waist area by adhering a polyethylene film layer over the fluff or absorbent layer at the cut forming the waist band. The adhesive is typically applied at the bond between the poly waste shield and the poly backing, forming an overlapping layer that prevents wicking from the absorbent layer past the waist band to the exterior of the diaper.

TEST PROCEDURES

The following test procedures were used to test the Examples that follow the procedures.

A Creep Resistance of Elastic Attachment and Multipurpose Adhesives

This test is used to evaluate an adhesive's ability to withstand the stress imparted on the glue line by the elastic when held in an elongated state at the use temperature of the disposable article.

Materials and Equipment

1. Multibead applicator similar to Meltex CT-225 having adjustable temperature, web speed, application rate, elastic attachment tensioning device and nip pressure.
2. Oven capable of maintaining 37° C. (100° F.) for 4 hours.
3. ¾" plywood, 12" wide and 12" long.
4. 300 mm ruler.
5. Natural rubber elastic.
6. Polyethylene film
7. Stapler.

Procedure

Remove operator side nozzle from the multibead applicator and adjust the elastic attachment tensioning device such that the elastic passes under but does not touch this orifice Adjust the tensioning device so that the elastic will be laminated to the polyethylene film at 100% stretch.

| Preferred Meltex Settings: | |
|---|---|
| Temperature | 150° C. (300° F.) |
| Nip Pressure | 4.0 bar (60 psi.) |

| -continued | |
|---|---|
| Preferred Meltex Settings: | |
| Application Rate | 7.0 mg/inch |
| Rewind and Unwind Tension | As low as possible |
| Web Speed | 45 ± 5 meter/min. |

Use the following equation to determine either flow rate or web speed:

$$\text{Web Speed (M/min.)} = \frac{\text{Flow Rate (g/min.)}}{(0.007 \text{ g/in.})(39.4 \text{ in/M})}$$

Run several meters of good application at 7.0 mg/in. coat weight. Allow the elastic/polyethylene laminate to contract and equilibrate at 25° C. overnight prior to testing.

Sample Preparation for Creep Testing at 37° C.

A. Using the 300 mm ruler, mark a line 290 mm from the end of the 12"×12"×¾" plywood. Mark another line 300 mm from the same end.

B. Peel the elastic away from one end of the polyethylene enough to facilitate stapling through the poly into the end of the plywood. Stretch the laminate until the polyethylene is ungathered but not stretched. Mark the elastic at the 300 mm line. Allow the laminate to contract until the mark on the elastic is over the 290 mm line an staple through the polyethylene to secure the other end of the laminate. You now have a laminate that is fixed at 97% of full extension of the elastic.

C. Peel the elastic back from the poly at one end of the edge of the plywood board Peel the other end to the 290 mm line.

D. Prepare 5 specimens per adhesive tested.

TEST PROCEDURE

A. Preheat oven to 37° C. Prepare test specimens per above instructions.

B. Place plywood with attached test specimens in oven and note the time.

C. After 4 hours remove plywood and measure the length of elastic that is still glued down to the polyethylene.

Use the following equation to calculate the % creep;.

$$\% \text{ Creep} = \frac{\text{Original length} - \text{Length after}}{\text{Original length (290 mm)}} \times 100$$

B. DYNAMIC PEEL AND STATIC SHEAR TESTS FOR MULTIBEAD ADHESIVES

SCOPE

Static Shear

This test is an indication of an adhesive's ability to withstand bond failure under a constant load at a temperature approximating the use temperature of a disposable article.

Dynamic Peel

This test is used to determine the bonding strength of an adhesive when subjected to a dynamic peel force.

Materials and Equipment

1. Multibead applicator similar to Meltex CT-225 having adjustable temperature, web application rate and nip pressure.
2. Suitable force measuring device (i.e., Instron or I-Mass).
3. Programmable oven capable of maintaining 37° C. (100° F.) for 8 hours and registering failure times.
4. 50 gram mass equipped with mechanical means of attaching to samples.
5. Release paper cut into 2"×8" strips.
6. Nonwoven fabric and polyethylene film.

Procedure

Adjust multibead applicator to proper settings. Preferred settings are shown below. Adjustments can be made based on the type of adhesive or application. Normally, beads should be applied to the treated side of the poly and nipped to the nonwoven or other substrate.

| Preferred Multibead Settings: | |
|---|---|
| Temperature | 275° F., 300° F. |
| Nip Pressure | 1.4 bar (20 psi), |
| Application Rate | 1.6 mg/inch/bead |
| Swivel Roll | Applied, but no pressure |
| Rewind and Unwind Tension | As low as possible |
| Web Speed | 45 ± 5 meters/min. |

Use the following equation to determine either flow rate or web speed.

$$\text{flow rate (g/min)} = \frac{(\text{web speed (39.4 (App. M/min)) (in/M)) rate})}{(\text{g/in/bd})(\text{\# of beads})}$$

Run several meters of good application at 1.6 mg/inch/bead coat weight. During the run, drop in 8-10 strips of release paper. Make sure they are applied as straight across the bead as possible.

1. Procedure for Static Shear

A. Sample preparation—mark along the bond line at 1 inch intervals. Cut across 3 bond lines at these intervals. Cut off the PE at one end and NW at the other end resulting in a typical shear sample.
Prepare 7-8 samples B. Test procedure—preheat oven to 100° F. Preclamp all samples to be tested to a 50 gram mass. Hang all samples in oven as quickly as possible. Take care to insure that all samples hang freely and do not interfere with each other. Close oven, note starting time, and record failure times.

2. Procedure for Dynamic Peel

A. Sample preparation—cut across the bond lines in the middle of the release paper. Then cut out about 3 inches of a 1 inch wide strip containing 1 bead. The resulting strip should have 1 inch of release paper and 2 inches of a single bead. Prepare 7-8 samples.

B. Test procedure—run T-peels on 7-8 samples at room temperature using a crosshead speed of 1 in/min., 25 seconds dwell time. Start crosshead and run for 10 seconds and then reset the counter for 25 more seconds. Use this average for the peel value.

Report

1. Static Shear

Average elapsed hang time (in minutes).
Failure mode (adhesive vs. substrates).
Additional descriptive statistics and pertinent information such as adhesive I.D., application temperature, nip pressure, application rate.
Samples that sustain 480 minutes of loading should be recorded as such and noted as "did not fail".

2. Dynamic Peel

Average maximum force to rupture (in grams).
Failure mode (adhesive, substrate or cohesive).
Additional descriptive statistics and pertinent information as described above.

COMPARATIVE EXAMPLE A

Using a sigma blade mixer an adhesive for elastic attachment was selected from Puletti, U.S. Pat. No. 4,419,494.

TABLE 2

| Ingredient | Name | Percent |
|---|---|---|
| A-B-A block copolymer | KRATON 1102 | 30.0 |
| A-B-A block copolymer | KRATON 1111 | 5.0 |
| Tackifying resin | FORAL 105 | 38.5 |
| Tackifying resin | ESCOREZ 5320 | 20.0 |
| Plasticizing oil | KAYDOL | 5.0 |
| Antioxidant blend | (IRGANOX 1010 & 1076) | 2.0 |

COMPARATIVE EXAMPLE B

Using standard hot melt processing technology, the following multi-line adhesive was prepared from Schmidt, U.S. Pat. No. 4,526,557.

TABLE 3

| Ingredient | Name | Percent |
|---|---|---|
| Multiblock A-B-A-B-A-B block copolymer | STEREON 840A | 20.0 |
| Tackifier | ZONATAC 105 LITE | 60.0 |
| Plasticizing oil | White USP Mineral Oil | 20.0 |
| Antioxidant | IRGANOX 1010 | 0.1 |

The adhesives of Table 6, No. 1, Comparative Example A and B were tested for viscosity, color, static shear, softening point, SAFT and creep resistance at 100° F. The results of that testing is shown in the following table.

TABLE 4

| | Example B | Adhesive of Table 6, No. 1 | Example A |
|---|---|---|---|
| Brookfield Viscosity spindle SC4-21 | | | |
| at 250° F. | 11,240 cP | 12,700 cP | 341,000 cP |
| at 275° F. | 5,430 cP | 6,300 cP | 145,000 cP |
| at 300° F. | 2,970 cP | 3,150 cP | 73,000 cP |
| at 325° F. | 1,768 cP | 1,875 cP | 41,400 cP |
| at 350° F. | 1,170 cP | 1,200 cP | 24,900 cP |
| Gardner Color | 2-3 | 3-4 | 12-13 |
| Multiline Static Shears at 100° F. | 143 min. | 326 min. | N/A* |
| Mettler Soft. Pt. | 170° F. | 187° F. | 211° F. |
| SAFT | | 165° F. | 177° F. |
| Creep Resistance of elastic attachment at 100° F. | 71% | 5% | 77.5% |
| Peel test** | 105/110° F. | 110/115° F. | N/A* |

TABLE 4-continued

|  | Example B | Adhesive of Table 6, No. 1 | Example A |
|---|---|---|---|
| Dynamic Peel Adhesion | Cohesive failure (123 gms) | Substrate failure | N/A |
| Storage at 140° F. | total delamination | no delamination | N/A |

*The high viscosity adhesive intermittently clogged the extruder nozzle and when not clogging the adhesive did not machine well - it did not form a fine line extrudate.
**(Pass/Fail, see Schmidt, U.S. Pat. No. 4,526,577 Crossmachine direction.) Bonds were made on a Meltex CT-25 according to procedures outlined in the static shear test method at a coat weight of 1.6 g/min.

The data recorded in Table 4 comparing a standard elastic attachment adhesive (Comparative Example A) and a standard multi-line construction adhesive (Comparative Example B) with the adhesive of Table 6, No. 1 of the invention shows that the invention in comparison to the Comparative Examples provides superior multi-line construction and elastic band attachment properties.

With respect to the multi-line construction properties of the adhesives, applicant's adhesive is a significant improvement over the multi-line adhesive disclosed in the Schmidt patent The multi-line static shear test indicates that the multi-line bond between the polyethylene film and nonwoven has a much greater resistance to shear at body temperature, indicating that the disposable article made with the adhesive of the invention would be much more likely to retain its mechanical integrity while worn. The dynamic peel adhesion test indicates that the Schmidt adhesive bond between nonwoven and polyethylene is subject to adhesive failure, while the adhesive of the invention maintains the integrity of the bond until the substrate itself fails. Such a result additionally indicates that the adhesive bond is more likely to survive during use. The storage test at 140° F. indicates that the adhesives of the invention when compared to the Schmidt adhesive are . much more likely to retain an intact construction during high temperature storage. Should the disposable articles be subject to high temperature during storage and transportation, articles made with the adhesive of the invention are much more likely to maintain structural integrity of the elastic. The articles made using the Schmidt adhesive suffer the drawback that the elastic may no longer be bonded to the polyethylene backing sheet if stored at 140° F.

With respect to elastic attachment properties, Example A and Example B have a creep failure of the elastic attachment of 77.5% and 71%, respectively, indicating that the elastic once bonded to the polyethylene backing sheet could lose a substantial proportion of its stretch during use. In comparison, the adhesive of the invention loses only 5% of its stretch at these test conditions. Such test results indicate that once applied to the polyethylene backing sheet, the elastic using the adhesive of the invention is securely bonded and has very little movement These results indicate that when used in a disposable diaper, the elastics used in either a leg opening or waistband would maintain a tight, secure fit because the elastics were maintained in a correct position. When using the adhesives of the Puletti patent, the elastic may not remain fully fixed to the poly resulting in a loose, unacceptable fit.

EXAMPLE I

In a Baker-Perkins twin screw 80 millimeter compounder extruder having 2 feed ports and maintained at 275° F., approximately equal volumes of radial block copolymer (KRATON D 1184) and tackifying resin (ZONATAC 105) were blended using established extrusion processing techniques as described in "Continuous Production of Hot Melt Adhesives, Aspects of Quality and Coating", at a rate of 300 lbs. per hour by adding the copolymer and a portion of resin to a feed port and the remaining resin through a second feed port. The blended rubber/resin mixture is . extruded through a three die section with multiple circular ports and is pelletized under 50° F. water. The pelletized preblend is treated with an aqueous talc dispersion (about 1 wt % in water) to reduce blocking.

EXAMPLE II

Example I was repeated except that the pellets are dusted with talc to reduce blocking at a weight add-on of about 0.07 wt % talc.

EXAMPLE III

In a Baker-Perkins twin screw compound extruder having two feed ports and a single screw side stuffer at 275° F. at 300 lbs. per hour manufacturing rate, an adhesive preblend of the following composition is made:

TABLE 5

| Ingredient | Preblend I Name | Parts (Wt.) |
|---|---|---|
| Radial block polymer | K 1184 | 1 |
| Tackifier | ZONATAC 105 | 1.5 |

The composition was pelletized in 90° F. water containing approximately 1 wt % talc resulting in a talc coating add-on of about 0.07 wt %.

Into a heated sigma blade mixer was placed 19.6 parts of TUFFLO 6056 oil, 0.5 parts of WESTON 619 antioxidant and 26.0 parts of Preblend I. The contents of the mixer were agitated until uniform and into the mixer was placed 53.3 parts of the tackifying resin (PERMALYN 305). This adhesive is shown as No. 1 in Table 6.

The following Table 6 sets forth adhesives and test results comparing the adhesives of the invention to adhesives of the prior art based on STEREON 840A and KRATON 1111 and 1102 polymer.

TABLE 6

|  | 1 | 2 | 3 | 4 | 5 | 6 | 7 | 8 | 9 | 10 | 11 | 12 |
|---|---|---|---|---|---|---|---|---|---|---|---|---|
| KRATON D-1184 | 9.5 | 10.64 |  |  |  | 20.0 |  |  |  |  |  |  |
| STEREON 840 A |  |  | 10.0 |  |  |  | 20.0 |  |  | 30.0 |  |  |
| KRATON 1102 |  |  |  | 10.0 |  |  |  | 20.0 |  |  | 30.0 |  |
| KRATON 1111 |  |  |  |  | 10.0 |  |  |  | 20.0 |  |  | 30.0 |
| PERMALYN | 51.9 | 53.3 | 54.5 | 54.5 | 54.5 | 44.5 | 44.5 | 44.5 | 44.5 | 34.5 | 34.5 | 34.5 |

TABLE 6-continued

|  | 1 | 2 | 3 | 4 | 5 | 6 | 7 | 8 | 9 | 10 | 11 | 12 |
|---|---|---|---|---|---|---|---|---|---|---|---|---|
| 305 | | | | | | | | | | | | |
| ZONATAC 501 | 14.3 | 15.96 | 15.0 | 15.0 | 15.0 | 15.0 | 15.0 | 15.0 | 15.0 | 15.0 | 15.0 | 15.0 |
| WESTON 619 | 0.5 | 0.5 | | | | | | | | | | |
| IRGANOX 1076 | | | 0.5 | 0.5 | 0.5 | 0.5 | 0.5 | 0.5 | 0.5 | 0.5 | 0.5 | 0.5 |
| TUFFLO 6056 | 19.0 | 19.6 | 20.0 | 20.0 | 20.0 | 20.0 | 20.0 | 20.0 | 20.0 | 20.0 | 20.0 | 20.0 |
| PETROLITE E-1040 | 4.8 | | | | | | | | | | | |
| Visc. cP at 275° F. | 6,300 | 8,350 | 950 | 1,125 | 1,188 | 186,000 | 4,250 | 6,250 | 6,200 | 16,400 | 20,000 | 25,200 |
| Creep resistance, % 4 hrs. at 100° F. | 5 | 30 | 100 | 100 | 100 | | 87 | 99.7 | 78.4 | AFP 100 | AFP 100 | AFP 100 |
| Dynamic peel adhesion | SSF | SSF | CF 69 gm | CF 44 gm | CF 32 gm | | SSF | SSF | SSF | AFN 49 gm | AFN 14 gm | AFP 27 gm |
| Static shear at 100° F. (min.) | 326 | 161 | 136 | 28 | 75 | | 84 | 128 | 176 | 49 | 219 | 509 |
| Storage at 140° F. | no change at 24 hrs. | slight change at 24 hrs.* | total delam. | total delam. | total delam. | | total delam. | total delam. | total delam. | total delam. | total delam. | total delam. |

\* = Slight delamination at edge
SSF = Substrate failure
CF = Cohesive failure
AFN = Adhesive failure to nonwoven
AFP = Adhesive failure to polyethylene Table 6 compares adhesives prepared with KRATON D 1184, a preferred high molecular weight radial block copolymer of the invention and comparison adhesives prepared from STEREON 840A (a linear multi-block A-B-A-B-A-B copolymer), KRATON 1102, and KRATON 1111 (two linear A-B-A block copolymers). The adhesives are compared at amounts ranging from about 10 to about 30 parts of polymer per about 100 parts of adhesives These data clearly show that the adhesives made with KRATON D1184 are different and superior to conventional adhesives in adhesive properties. These superior properties are obtained from a polymer with a substantially different function, at substantially differing proportions to provide substantially different test results.

The high molecular weight radial block copolymers of the invention function substantially differently than the polymers disclosed in the Schmidt patent. The Schmidt polymers are low molecular weight polymers having a molecular weight of less than 140,000 and the Schmidt patent is primarily directed to the linear A-B-A and A-B-A-B-A-B block copolymer. These differences between the high molecular weight radial block copolymers of the invention and the polymers of the Schmidt application result in the use of substantially reduced proportions of polymer that surprisingly give results that are superior to the Schmidt adhesives in a multi-line construction mode and provide an elastic attachment property that is lacking in the Schmidt adhesive materials.

Clearly only the KRATON D1184 adhesives containing less than about 15 wt % of the high molecular weight radial block copolymer contained sufficient properties to enable manufacture of disposable articles using the adhesive in both a multi-line and elastic attachment mode.

In the dynamic peel adhesion test, adhesives prepared using the linear block copolymers of the Schmidt patent provide adequate properties only at amounts of the polymer that approximate 20 wt %. At lesser proportions the adhesive fails cohesively. At greater proportions, 30%, the adhesive fails adhesively either the nonwoven or the polyethylene backing sheet. In sharp contrast, the adhesive of the invention using the high molecular weight radial block copolymers at amounts resulting in cohesive failure in the adhesives of the invention produce an adhesive bond stronger than the substrate which adhesive does not fail at test conditions.

In the elastic attachment mode, the adhesives prepared using the low molecular weight linear block copolymers fail to provide creep resistance. Additionally the adhesives of the Schmidt patent made with 30 wt % of the prior art linear copolymers fail adhesively to the polyethylene backing sheet. The Schmidt adhesives fail to provide adhesion in the creep mode under stress. These adhesives also fail in an unstressed mode by losing bond integrity at 140° F. under storage conditions. Only the adhesives made with the high molecular weight radial block copolymer provide adequate bond strength to maintain the elastic in a stretched configuration on the disposable article or in a high temperature unstressed storage environment.

With respect to adhesive viscosity, it is important to note that the viscosity of the adhesive of the invention . No. 1 has a viscosity suitable for both multi-line and elastic attachment procedures. The adhesive in Table 6, No. 6 made with 20 wt % of the high molecular weight radial block copolymers results in a viscosity that is too high for either elastic attachment or multi-line properties. While at the same loading, the adhesives made with conventional low molecular weight polymers have a viscosity useful in multi-line construction techniques.

We have shown in the above discussion and tables of data that the adhesive of this invention is a superior multi-line/elastic attachment material. Additionally they are superior to standard prior art multi-line adhesives that are exemplified in Table 6 which typically contains substantially more polymer at increased cost.

TABLE 7

|  | 1 | 2 |
|---|---|---|
| KRATON 1184 | 9.12 | 9.12 |
| KRATON 1117 | 4.9 | 4.9 |
| ZONATAC 501 | 13.18 | 13.18 |
| KAYDOL MINERAL OIL | 19.4 | 19.4 |
| WESTON 619 | 0.5 | 0.5 |
| PERMALYN 305 | 47.9 | 49.9 |
| AC-9 | 5.0 |  |
| PETROLYTE E-1040 |  | 3.0 |
| Creep resistance 4 hrs. at 100° F. | 3.0% | 11.4% |
| Static shear at 100° F. | 275 min. | 260 min. |
| Viscosity at 275° F. | 12,875 cP | 9,325 cP |
| Storage at 140° F. | No change | No change |
| Dynamic Peel Adhesion | SSF | SSF |

SSF = Substrate failure
CF = Cohesive failure

Table 7 shows that the use of other block copolymers in combination with a high molecular weight radial polymer will result in adhesive with improved properties over the prior art.

In view of the disclosure and data in this case and particularly in view of Tables 4, 6 and 7, we have shown that the adhesive compositions of this invention are prepared from polymers having substantially different functions than that disclosed in the Schmidt and Puletti patents. Further the adhesive properties are obtained in a substantially different way, i.e. with different proportions. Lastly, the resulting properties are substantially different in that the adhesives of the invention are superior to the Schmidt materials in construction properties and possess properties not present in the Schmidt adhesives. Namely the adhesive compositions are useful as elastic attachment adhesives while the Schmidt adhesives fail in this application.

The above discussion provides a basis for understanding the spirit and scope of the invention. However, since many embodiments of the invention can be made obtaining the benefits of the invention, the invention resides in the claims hereinafter appended.

I claim:

1. A hot melt adhesive composition for the construction of disposable articles which comprises:
   (a) 5 to 14 wt % of a radial block copolymer having a molecular weight of at least 145,000 having the formula:

$(A—B)_n—Y$ wherein Y is a multivalent coupling agent, A comprises a polyvinyl substituted aromatic block, B comprises a polymeric rubbery midblock, and n comprises an integer of at least 3;
   (b) about 45 to 85 wt % of a compatible tackifying agent selected from the group consisting of a $C_5$ resin, a styrenated $C_5$ resin, a styrenated terpene resin, a hydrogenated $C_9$ resin, a rosin derivative, a styrenated terpene resin and mixtures thereof; and
   (c) about 5 to 35 wt % of a plasticizing oil; wherein the hot melt pressure sensitive adhesive has a static shear at 100° F. of at least 30 min., a creep resistance at 100° F. of less than about 30% and exhibits a viscosity of less than 25,000 cP at 275° F.

2. The adhesive of claim 1 wherein A comprises a polystyrene block and B comprises a hydrogenated or non-hydrogenated polymeric block comprising butadiene, isoprene or mixtures thereof.

3. The adhesive of claim 2 wherein B comprises a polybutadiene block.

4. The adhesive of claim 2 wherein B comprises a polyisoprene block.

5. The adhesive of claim 1 wherein the plasticizing oil comprises a naphthenic, a paraffinic oil or mixtures thereof.

6. The adhesive of claim 1 wherein the viscosity comprises 5,000 to 10,000 cP at 275° F.

7. The composition of claim 1 wherein the creep resistance at 100° F. comprises about 5 to 25%.

8. The adhesive of claim 1 wherein the dynamic peel adhesion test results in substrate failure.

9. The adhesive of calm 2 wherein the adhesive additionally comprises 0.1 to 10 wt % of a linear A-B-A block copolymer wherein A comprises a polystyrene block and B comprises a polymeric rubbery midblock comprising butadiene, isoprene, or mixtures thereof.

10. A hot melt pressure sensitive adhesive composition for the multi-line construction of disposable articles which consists essentially of:
   (a) about 5 to 14 wt % of a radial block copolymer having a molecular weight of about 185,000 to 240,000 having the formula:

$(A—B)_n—Y$ wherein Y is a multivalent coupling agent, A comprises a polystyrene block, B comprises a polymeric butadiene midblock, and n comprises an integer of about 3 to 5;
   (b) about 0.1 to 10 wt % of a linear A-B-A block copolymer wherein A is polystyrene blend and B comprises polybutadiene block or polyisoprene block;
   (c) about 40 to 80 wt % of a compatible tackifying agent selected from the group consisting of a $C_5$ resin, a styrenated $C_5$ resin, a styrenated terpene resin, a hydrogenated $C_9$ resin, a rosin derivative, a styrenated terpene resin and mixtures thereof; and
   (d) about 5 to 35 wt % of a plasticizing oil; wherein the hot melt pressure sensitive adhesive has a static shear of at least about 30 min. at 100° F., a creep resistance of at least about 30% at 100° and exhibits a viscosity of less than 15,000 cP at 275° F.

* * * * *